(12) United States Patent
Bigsby et al.

(10) Patent No.: US 7,914,584 B2
(45) Date of Patent: Mar. 29, 2011

(54) PROSTHESIS SYSTEM WITH TRUNNION AND REMOVABLY COUPLED HEAD

(75) Inventors: Robert John Andrew Bigsby, Penarth (GB); Robert Andrew Scott, Chippenham (GB)

(73) Assignee: Biomet Manufacturing Corp., Warsaw, IN (US)

( * ) Notice: Subject to any disclaimer, the term of this patent is extended or adjusted under 35 U.S.C. 154(b) by 465 days.

(21) Appl. No.: 11/255,158

(22) Filed: Oct. 20, 2005

(65) Prior Publication Data

US 2006/0106463 A1    May 18, 2006

(51) Int. Cl.
*A61F 2/32* (2006.01)
(52) U.S. Cl. .................. 623/22.42; 623/22.43; 623/22.4
(58) Field of Classification Search ...... 623/22.4–23.89; A61F 2/32
See application file for complete search history.

(56) References Cited

U.S. PATENT DOCUMENTS

| | | | |
|---|---|---|---|
| 4,051,559 A | 10/1977 | Pifferi | |
| 4,068,324 A | 1/1978 | Townley et al. | |
| 4,141,088 A | 2/1979 | Treace et al. | |
| 4,167,047 A | 9/1979 | Grundei et al. | |
| 4,404,691 A | 9/1983 | Buning | |
| 4,406,023 A | 9/1983 | Harris | |
| 4,488,319 A | 12/1984 | von Recûm | |
| 4,549,319 A | 10/1985 | Meyer | |
| 4,551,863 A | 11/1985 | Murray | |
| 4,578,081 A | 3/1986 | Harder et al. | |
| 4,608,055 A | 8/1986 | Morrey et al. | |
| 4,642,124 A | 2/1987 | Cooke | |
| 4,657,551 A | 4/1987 | Ecke | |
| 4,657,552 A | 4/1987 | Karpf | |
| 4,670,015 A | 6/1987 | Freeman | |
| 4,704,128 A | 11/1987 | Frey | |
| 4,718,912 A | 1/1988 | Crowninshield | |
| 4,728,335 A | 3/1988 | Jurgutis | |
| 4,738,681 A | 4/1988 | Koeneman et al. | |
| 4,753,657 A | 6/1988 | Lee et al. | |
| 4,764,171 A | 8/1988 | Harder et al. | |
| 4,778,475 A | 10/1988 | Ranawat et al. | |
| 4,790,852 A | 12/1988 | Noiles | |
| 4,790,854 A | 12/1988 | Harder et al. | |
| 4,795,469 A | 1/1989 | Oh | |
| 4,813,959 A | 3/1989 | Cremascoli | |
| 4,813,963 A | 3/1989 | Hori et al. | |

(Continued)

FOREIGN PATENT DOCUMENTS

DE    199 28 709    1/2001

(Continued)

OTHER PUBLICATIONS

"Alliance Hip Systems X-Series Bi-Metric Porous Primary Hip System" brochure, Biomet Orthopedics, Inc. copyright 2002.

(Continued)

*Primary Examiner* — David Isabella
*Assistant Examiner* — Jason-Dennis Stewart
(74) *Attorney, Agent, or Firm* — Harness, Dickey

(57) ABSTRACT

A prosthesis includes a trunnion having a first end defining a uniform cross-section and a second end adapted to be fixed to a prosthesis stem. A ceramic head has a first bearing surface on which a second prosthesis fixed to a second bone can articulate. The ceramic head defines a recess. The first end of the trunnion is fixedly received within the recess. The second end of the trunnion is releasably connectable to the prosthesis stem by a taper connection.

9 Claims, 2 Drawing Sheets

U.S. PATENT DOCUMENTS

| | | | |
|---|---|---|---|
| 4,822,370 A | 4/1989 | Schelhas | |
| 4,840,632 A | 6/1989 | Kampner | |
| 4,842,606 A | 6/1989 | Kranz et al. | |
| 4,846,839 A | 7/1989 | Noiles | |
| 4,851,007 A | 7/1989 | Gray | |
| 4,865,609 A | 9/1989 | Roche | |
| 4,878,917 A | 11/1989 | Kranz et al. | |
| 4,904,263 A | 2/1990 | Buechel et al. | |
| 4,917,530 A | 4/1990 | Engelhardt et al. | |
| 4,919,670 A | 4/1990 | Dale et al. | |
| 4,938,770 A | 7/1990 | Frey et al. | |
| 4,944,761 A | 7/1990 | Stuhmer et al. | |
| 4,957,510 A | 9/1990 | Cremascoli | |
| 4,963,155 A * | 10/1990 | Lazzeri et al. | 623/22.42 |
| 4,964,869 A * | 10/1990 | Auclair et al. | 623/22.43 |
| 4,976,740 A | 12/1990 | Kleiner | |
| 4,978,359 A | 12/1990 | Wilhelm et al. | |
| 4,995,883 A | 2/1991 | Demane et al. | |
| 5,002,578 A | 3/1991 | Luman | |
| 5,004,475 A | 4/1991 | Vermeire | |
| 5,004,476 A | 4/1991 | Cook | |
| 5,047,060 A | 9/1991 | Henssge et al. | |
| 5,080,685 A | 1/1992 | Bolesky et al. | |
| 5,100,407 A | 3/1992 | Conrad et al. | |
| 5,108,449 A | 4/1992 | Gray | |
| 5,108,451 A | 4/1992 | Forte | |
| 5,116,379 A | 5/1992 | McLardy Smith | |
| 5,133,770 A | 7/1992 | Zweymüller et al. | |
| 5,135,529 A | 8/1992 | Paxson et al. | |
| 5,156,624 A | 10/1992 | Barnes | |
| 5,156,627 A | 10/1992 | Amstutz et al. | |
| 5,171,275 A | 12/1992 | Ling et al. | |
| 5,171,324 A | 12/1992 | Campana et al. | |
| 5,181,928 A | 1/1993 | Bolesky et al. | |
| 5,286,260 A | 2/1994 | Bolesky et al. | |
| 5,290,318 A | 3/1994 | Ling et al. | |
| 5,314,479 A | 5/1994 | Rockwood, Jr. et al. | |
| 5,342,366 A | 8/1994 | Whiteside et al. | |
| 5,370,698 A | 12/1994 | Heimke et al. | |
| 5,370,706 A | 12/1994 | Bolesky et al. | |
| 5,387,244 A | 2/1995 | Breard | |
| 5,405,403 A | 4/1995 | Mikhail | |
| 5,413,610 A | 5/1995 | Amino et al. | |
| 5,456,717 A | 10/1995 | Zweymuller et al. | |
| 5,458,651 A | 10/1995 | Lawes | |
| 5,480,451 A | 1/1996 | Grundei et al. | |
| 5,507,830 A | 4/1996 | DeMane et al. | |
| 5,507,833 A | 4/1996 | Bohn | |
| 5,580,352 A | 12/1996 | Sekel | |
| 5,653,764 A | 8/1997 | Murphy | |
| 5,653,765 A | 8/1997 | McTighe et al. | |
| 5,658,352 A | 8/1997 | Draenert | |
| 5,728,161 A | 3/1998 | Camino et al. | |
| 5,766,263 A | 6/1998 | Grundei et al. | |
| 5,800,560 A | 9/1998 | Draenert | |
| 5,876,456 A | 3/1999 | Sederholm et al. | |
| 5,876,459 A | 3/1999 | Powell | |
| 5,906,644 A * | 5/1999 | Powell | 623/20.15 |
| 5,931,871 A | 8/1999 | Baur et al. | |
| 6,048,365 A | 4/2000 | Burrows et al. | |
| 6,136,035 A | 10/2000 | Lob et al. | |
| 6,139,583 A | 10/2000 | Johnson | |
| 6,168,632 B1 | 1/2001 | Moser et al. | |
| 6,190,416 B1 | 2/2001 | Choteau et al. | |
| 6,190,418 B1 | 2/2001 | Gerhardt | |
| 6,193,760 B1 | 2/2001 | Copf | |
| 6,197,062 B1 | 3/2001 | Fenlin | |
| 6,197,063 B1 | 3/2001 | Dews | |
| 6,200,350 B1 | 3/2001 | Masini | |
| 6,238,436 B1 | 5/2001 | Lob et al. | |
| 6,264,699 B1 | 7/2001 | Noiles et al. | |
| 6,299,648 B1 | 10/2001 | Doubler et al. | |
| 6,306,174 B1 | 10/2001 | Gie et al. | |
| 6,355,068 B1 | 3/2002 | Doubler et al. | |
| 6,361,566 B1 | 3/2002 | Al-Hafez | |
| 6,383,225 B2 | 5/2002 | Masini | |
| 6,383,227 B1 | 5/2002 | Baroud et al. | |
| 6,383,228 B1 | 5/2002 | Schmotzer | |
| 6,436,147 B1 | 8/2002 | Zweymüller | |
| 6,440,171 B1 | 8/2002 | Doubler et al. | |
| 6,464,728 B1 | 10/2002 | Murray | |
| 6,497,727 B1 | 12/2002 | Pope et al. | |
| 6,520,994 B2 | 2/2003 | Nogarin | |
| 6,524,343 B2 | 2/2003 | Storer et al. | |
| 6,540,788 B1 | 4/2003 | Zweymuller | |
| 6,613,092 B1 | 9/2003 | Kana et al. | |
| 6,613,094 B2 | 9/2003 | Zweymuller | |
| 6,679,890 B2 | 1/2004 | Margulies et al. | |
| 6,695,883 B2 | 2/2004 | Crofford | |
| 6,786,931 B2 | 9/2004 | Hazebrouck | |
| 6,800,095 B1 * | 10/2004 | Pope et al. | 623/23.11 |
| 6,997,958 B2 * | 2/2006 | Hassler et al. | 623/22.46 |
| 2001/0049561 A1 | 12/2001 | Dews et al. | |
| 2002/0007220 A1 | 1/2002 | Gie et al. | |
| 2002/0040244 A1 | 4/2002 | Despres, III et al. | |
| 2002/0099447 A1 | 7/2002 | Mears et al. | |
| 2002/0116067 A1 | 8/2002 | Mears et al. | |
| 2002/0120343 A1 | 8/2002 | Doubler et al. | |
| 2002/0128720 A1 | 9/2002 | Masini | |
| 2003/0014123 A1 | 1/2003 | Copf et al. | |
| 2003/0050704 A1 | 3/2003 | Keynan | |
| 2003/0074079 A1 * | 4/2003 | McTighe et al. | 623/22.42 |
| 2003/0074080 A1 | 4/2003 | Murray | |
| 2003/0074083 A1 * | 4/2003 | LeGros et al. | 623/23.35 |
| 2003/0088316 A1 | 5/2003 | Ganjianpour | |
| 2003/0109933 A1 | 6/2003 | Weissman et al. | |
| 2003/0158606 A1 | 8/2003 | Coon et al. | |
| 2003/0171819 A1 | 9/2003 | Sotereanos | |
| 2003/0204268 A1 | 10/2003 | Gerbec et al. | |
| 2003/0204269 A1 | 10/2003 | Gerbec et al. | |
| 2003/0220698 A1 | 11/2003 | Mears et al. | |
| 2004/0010319 A1 | 1/2004 | McTighe et al. | |
| 2004/0030401 A1 | 2/2004 | Hassler et al. | |
| 2004/0044415 A1 | 3/2004 | Zwemuller | |
| 2004/0138757 A1 | 7/2004 | Nadzadi et al. | |
| 2004/0143335 A1 | 7/2004 | Dews et al. | |
| 2004/0162621 A1 | 8/2004 | Crofford | |
| 2004/0236430 A1 | 11/2004 | Koch et al. | |
| 2004/0243246 A1 | 12/2004 | Lyren | |
| 2005/0043811 A1 * | 2/2005 | Doubler et al. | 623/22.42 |

FOREIGN PATENT DOCUMENTS

| | | |
|---|---|---|
| EP | 0032165 | 7/1981 |
| EP | 0 201 407 | 11/1986 |
| EP | 0 202 141 | 11/1986 |
| EP | 0 310 566 | 12/1993 |
| EP | 1 062 923 | 12/2000 |
| EP | 1 350 486 | 10/2003 |
| FR | 2 429 010 | 1/1980 |
| FR | 2 626 168 | 7/1989 |
| FR | 2 631 543 | 11/1989 |
| FR | 2 640 497 | 6/1990 |
| FR | 2 666 737 | 3/1992 |
| FR | 2 701 835 | 9/1994 |
| FR | 2 753 081 | 3/1998 |
| FR | 2 827 155 | 1/2003 |
| GB | 1 511 631 | 5/1978 |
| GB | 2 033 755 | 5/1980 |
| GB | 2260705 A | 4/1993 |
| GB | 2 366 733 | 3/2002 |
| WO | WO 01/13824 | 3/2001 |
| WO | WO 03/047471 | 6/2003 |

OTHER PUBLICATIONS

"Alliance Hip Systems", brochure, Biomet, Inc. copyright 1998.
"Alliance Instrumentation", brochure, Biomet, Inc. copyright 1998.
Anatomia e Malattie Degenerative Dell'Anca (Anatomy & Degenerative Hip Disease), C. Ruosi, et al. G.I.O.T. 2003; 29: 156-160.
"Answer Hip System Surgical Technique" brochure, Biomet Orthopedics, Inc. copyright 2001.
"Biomet Proximal Femoral Replacement" brochure, Biomet, Inc., copyright 1996.
"Finn Revision/Oncology Knee System" brochure, Biomet, Inc. copyright 1996.
"Impact Modular Hip Surgical Overview" brochure, Biomet Orthopedics, Inc. copyright 2001.

"Impact Modular Revision Surgical Technique" brochure, Biomet Orthopedics, Inc. copyright 2001.
"Impact Modular Total Hip System" brochure, Biomet, Inc. 23 sheets.
"Impact Modular Total Hip System" brochure, Biomet, Inc. copyright 1993.
"Implant Modular Total Hip System" brochure, Biomet, Inc. copyright 1992.
"Mallory Head Modular Calcar Surgical Technique" brochure, Biomet Orthopedics, Inc. copyright 2001.
"Mallory Head Porous Primary System," brochure, Biomet Orthopedics, Inc. copyright 2001.
"Mallory-Head Radial Acetabular Shell" Biomet, Inc., copyright 1998 2 sheets.
"Osteocap RS Hip System Surgical Technique" brochure, Biomet Orthopedics, Inc. copyright 2001.
"Patient-Matched Implants (PMI)" brochure, Biomet, Inc. copyright 1991.
"Replacement of the Proximal Humerus with a Ceramic Prosthesis: A Preliminary Report", Sim, et al. pp. 161-174, Clinical Orthopedics and Related Research.
"Stanmore Modular Hip System" brochure, Biomet, Inc. copyright 1998.
"Taperloc Hip System" brochure, Biomet, Inc. copyright 2000.
"The Asian Hip System" brochure, Biomet, Inc. copyright 1996.
Journal of Bone & Joint Surgery "Soft Tissue Balancing of the Hip, The Role of Femoral Offset Restoration," Charles, et al. J. Bone Joint Surg. Am. 86:1078-1088, 2004.
Ranawat/Burstein Total Hip System "Cemented Primary Series", brochure, Biomet, Inc. copyright 1994.
Ranawat/Burstein Total Hip System "Component Selection", brochure, Biomet, Inc. copyright 1992.
Ranawat/Burstein Total Hip System "Porous Primary Femoral Technique", brochure, Biomet, Inc. copyright 1995.
Ranawat/Burstein Total Hip System Porous Primary Series "The Metaphyseal Diaphyseal Fit", brochure, Biomet, Inc. copyright 1993.
Great Britain Office Action mailed Jul. 15, 2009 for GB0423415.9 to which the current matter claims benefit.

* cited by examiner

PROSTHESIS SYSTEM WITH TRUNNION AND REMOVABLY COUPLED HEAD

FIELD

This invention relates to prostheses and particularly but not exclusively relates to femoral hip prostheses.

INTRODUCTION

Total hip replacement surgery is a common procedure involving the removal of defective bone tissue on both sides of the hip joint and the subsequent implantation of acetabular and femoral prosthesis components. Some of the most commonly used femoral components comprise a metallic stem, about 150 mm in length, which is secured into the inermedullary cavity of the femur, extending along the femoral axis. A neck may be provided on the upper portion of the stem, in order to support a prosthetic femoral head. The superior portion of the neck forms a trunnion, allowing connection with the substantially spherical femoral head by means of a Morse taper. This type of connection permits the use of femoral heads formed from a range of different materials. One such material is alumina ceramic, preferred for its superior wear characteristics when articulating against polyethylene and ceramic acetabular prosthesis components.

A known technique for strengthening ceramic femoral heads includes the insertion of a metal bush into the tapered recess in the head. The Morse taper connection may be strengthened by the inclusion of the metal bush, however, significant hoop stresses may be generated within the ceramic component.

It is also known to construct a modular femoral prosthesis component, whereby a metal adaptor is used in place of the conventional femoral neck. The adaptor may be secured to the femoral head and to the supporting stem by means of standard Morse taper connections. This type of construction allows both the femoral head and the metal adaptor to be replaced during revision surgery without the need to disturb the implanted femoral stem.

SUMMARY

A prosthesis system can include a trunnion having a first end defining a substantially uniform cross-section and a second end adapted to be fixed to a prosthesis stem. A ceramic head has a first bearing surface on which a second prosthesis fixed to a second bone can articulate. The ceramic head can define a recess. The first end of the trunnion can be fixedly received within the recess. The second end of the trunnion can be releasably connectable to the prosthesis stem by a taper connection.

According to additional features, the second end of the trunnion can define a non symmetrical cross section. The trunnion includes an annular shoulder which defines a second bearing surface in a plane substantially perpendicular to a longitudinal axis of the first end of the trunnion. The head can further comprise an annular bearing surface and the first end of the trunnion can be permanently fixed within the recess of the head such that the second bearing surface on the trunnion abuts the annular bearing surface on the head. In one example the trunnion defines an arcuate contour along its longitudinal axis.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF PREFERRED EMBODIMENTS

The following description of the embodiment(s) is merely exemplary in nature and is in no way intended to limit the invention, its application, or uses. Moreover, while the description below is directed to a hip prosthesis, the same may be directed to an implant for any portion of the body.

Figure 1:
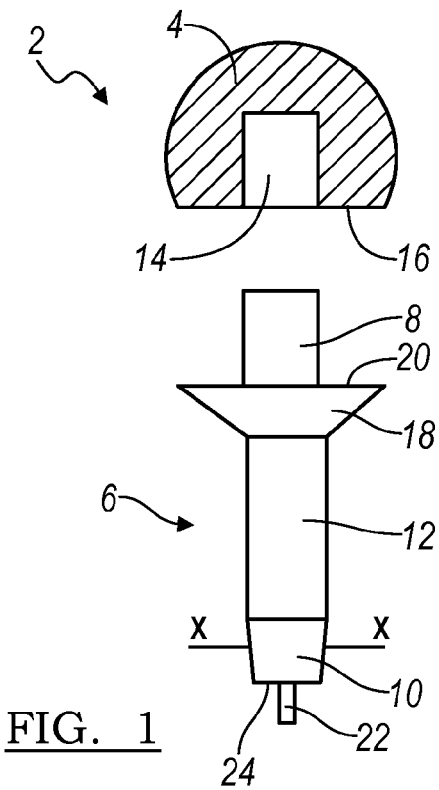
FIG. 1 shows two components of an exemplary hip prosthesis.

FIG. 1 shows an exemplary embodiment of a hip prosthesis 2 comprising a head 4 and a trunnion 6. The head 4 may be made from a ceramic material in the form of a partial sphere, which has a single planar surface 16. A cylindrical recess 14 extends into the head 4, from the planar surface 16 in a central position. The trunnion 6 may be made from metal and has a first end 8, a second end 10 and a midsection 12. The first end 8 of the trunnion 6 is a right circular cylinder. An annular shoulder 18 projects from the midsection 12, supporting a planar bearing surface 20. The second end 10 of the trunnion 6 may be tapered and has a non-rotationally symmetrical cross section XX. A pin 22 projects from the lower surface 24 of the second end 10. Alternatively, the second end 10 of the trunnion 6 may include a recess in the form of a blind bore.

Figure 2:
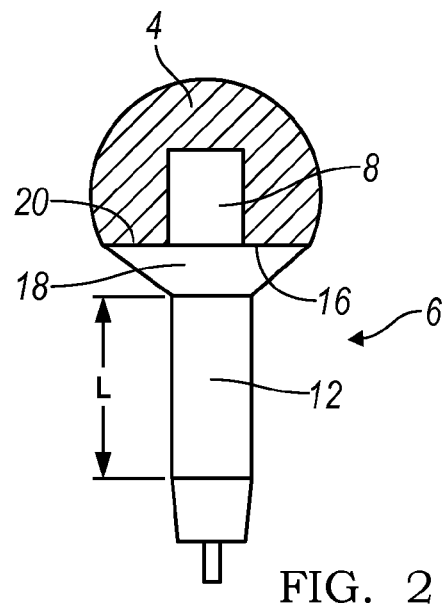
FIG. 2 shows the hip prosthesis components of FIG. 1 in an assembled position.

In FIG. 2, the two components of the hip prosthesis are shown in their assembled condition. The first end 8 of the trunnion 6 is received within the recess 14. The first end 8 may be permanently bonded in place any suitable method such as by adhesive or by brazing, which may include active alloy brazing. The dimensions of the recess 14 and the first end 8 of the trunnion 6 are such that the surface 16 of the head 4 abuts the surface 20 of the annular shoulder 18.

Figure 3:
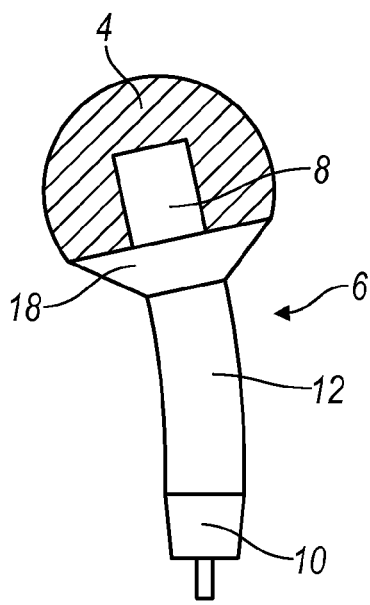
FIG. 3 shows a hip prosthesis according to another embodiment.

With reference to FIGS. 2 and 3, the midsection 12 of the trunnion 6 may be cylindrical and define a length L, which may be varied according to the particular needs of the patient. In another example, the midsection 12 may be curved, as shown in FIG. 3. The angle of curvature of the midsection 12 may also be varied according to the needs of the patient. The length and curvature of the midsection may be selected to provide the desired antiversion angle in the prosthetic joint.

Figure 4:
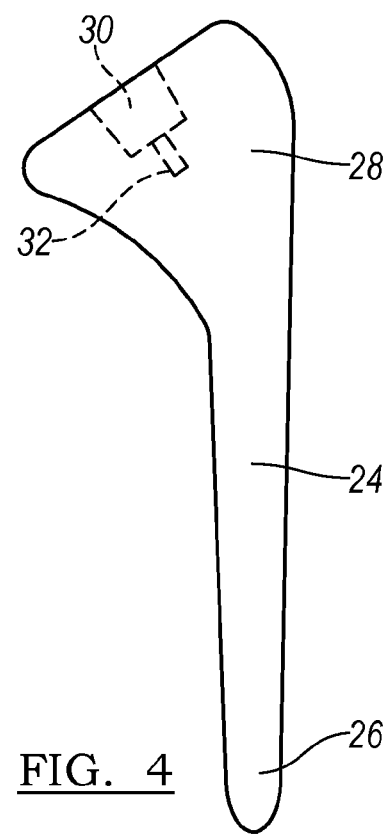
FIG. 4 shows an exemplary stem for use with the hip prosthesis of FIG. 1.

The assembled components of the prosthesis 2 are suitable for use in conjunction with a metallic stem 24, as shown in FIG. 4. The stem 24 has a linear portion 26 and a flared portion 28. A recess 30, in the form of a first blind bore, extends into the flared portion 28. A second recess 32, in the form of a second blind bore, extends from the base of recess 30. The recess 30 may be tapered or it may be cylindrical. Alternatively, a pin (not specifically shown) may protrude from the flared portion 28 of the stem 24.

Figure 5:
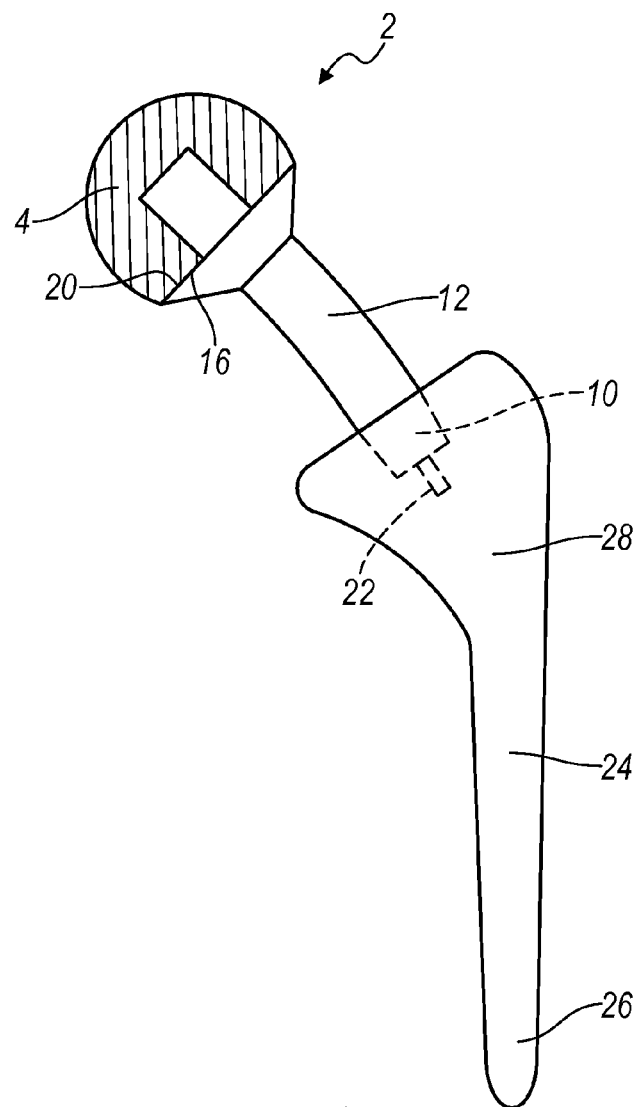
FIG. 5 shows the stem and prosthesis of FIG. 4 in an assembled position.

In use, the stem 24 may be implanted into the intermedullary cavity of the femur such that the flared portion 28 emerges at the level of a resected femoral neck. The prosthesis 2 may be secured to the stem 24, as shown in FIG. 5, by means of a taper connection between the second end 10 of the trunnion 6 and the recess 30. The taper connection may alternatively be formed between the recess formed in the second end 10 of the trunnion 6 and the pin protruding from the flared end 28 of the stem 24. In an assembled position, the pin 22 is received within the second recess 32 and acts as a centering device. The head 4 of the prosthesis 2 articulates within the shell of a corresponding acetabular implant (not shown). The surfaces 16 and 20 act as bearing surfaces for the transmission of forces generated in the joint.

The prosthesis components described may be supplied as a prosthesis kit. Each kit may be selected from a plurality of components including: femoral heads of varying diameters, trunnions of varying lengths and angles of curvature, and stems of varying sizes. The surgeon may then select the most appropriate combination of components for each individual patient in order to achieve a prosthesis that resembles the patient's original hip joint. Further, should problems be encountered during the positioning of the stem, misalignments can be corrected through the appropriate choice of trunnion.

While the invention has been described in the specification and illustrated in the drawings with reference to various embodiments, it will be understood by those skilled in the art that various changes may be made and equivalents may be substituted for elements thereof without departing from the scope of the invention as defined in the claims. Furthermore, the mixing and matching of features, elements and/or functions between various embodiments is expressly contemplated herein so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the teachings of the invention without departing from the essential scope thereof. Therefore, it is intended that the invention not be limited to the particular embodiment illustrated by the drawings and described in the specification as the best mode presently contemplated for carrying out this invention, but that the invention will include any embodiments falling within the foregoing description and the appended claims.

The invention claimed is:

1. A prosthesis system extending along a longitudinal axis and having a head assembly, comprising:
   a prosthesis stem;
   a trunnion having a first end and a second end and a midsection, the second end adapted to be fixed to the prosthesis stem, the midsection interposed between the head assembly and the prosthesis stem, the trunnion having an annular shoulder which defines a first bearing surface in a plane substantially perpendicular to the longitudinal axis of the first end of the trunnion, the annular shoulder also defining an outer surface that intersects the first bearing surface and extends outward from the longitudinal axis, the midsection being interposed between the annular shoulder and the second end, the midsection having a cross sectional area that is constant along an entire length of the midsection between the annular shoulder and the second end;
   a head having a second bearing surface on which a second prosthesis can articulate, and a third bearing surface, the head defining a recess adapted to securedly receive the first end of the trunnion such that the first bearing surface of the annular shoulder directly abuts the third bearing surface of head, the second bearing surface and the outer surface of the annular shoulder being continuous with respect to each other to cooperatively define the head assembly such that, in a cross section of the trunnion and the head taken along the longitudinal axis, the head defines an entirely curved line with two head end points and the shoulder defines two straight lines with respective shoulder end points, the two head end points being directly adjacent respective ones of the shoulder end points; and
   wherein the second end of the trunnion is releasably connectable to the prosthesis stem by a taper fit connection.

2. The prosthesis system of claim 1, wherein the longitudinal axis is curved along the midsection.

3. The prosthesis system of claim 1, wherein the first end of the trunnion is substantially cylindrical, such that the first end defines a substantially uniform cross-section along the entire longitudinal axis of the first end and the recess of the head is substantially cylindrical.

4. The prosthesis system of claim 1, wherein the second end of the trunnion is tapered.

5. The prosthesis system of claim 1, wherein the head is partially spherical, and the annular shoulder is frustoconical.

6. The prosthesis system of claim 1, wherein the outer surface of the annular shoulder is tapered, and wherein the third bearing surface of the head is annular.

7. The prosthesis system of claim 1, further comprising a plurality of trunnions and a plurality of heads, each trunnion and each head having at least one of a different size and a different shape.

8. The prosthesis system of claim 1, wherein the second end of the trunnion includes a pin that is received within the prosthesis stem, the pin centering the trunnion relative to the prosthesis stem when coupling the trunnion and the prosthesis stem.

9. A prosthesis system extending along a longitudinal axis and having a head assembly, comprising:
   a prosthesis stem;
   a trunnion having a first end and a second end and a midsection, the longitudinal axis curving along the midsection, the second end adapted to be fixed to the prosthesis stem, the midsection interposed between the head assembly and the prosthesis stem, the trunnion having an annular shoulder which defines a first bearing surface in a plane substantially perpendicular to the longitudinal axis of the first end of the trunnion, the annular shoulder also defining an outer surface that intersects the first bearing surface and extends outward from the longitudinal axis, the midsection being interposed between the annular shoulder and the second end, the midsection having a cross sectional area that is constant along an entire length of the midsection between the annular shoulder and the second end; and
   a head having a second bearing surface on which a second prosthesis can articulate, and a third bearing surface, the head defining a recess adapted to securedly receive the first end of the trunnion such that the first bearing surface of the annular shoulder directly abuts the third bearing surface of head, the second bearing surface and the outer surface of the annular shoulder being continuous with respect to each other to cooperatively define the head assembly such that, in a cross section of the trunnion and the head taken along the longitudinal axis, the head defines an entirely curved line with two head end points and the shoulder defines two straight lines with respective shoulder end points, the two head end points being directly adjacent respective ones of the shoulder end points;

wherein the second end of the trunnion is releasably connectable to the prosthesis stem by a taper fit connection, wherein the first end of the trunnion is substantially cylindrical, such that the first end defines a substantially uniform cross-section along the entire longitudinal axis of the first end and the recess of the head is substantially cylindrical, wherein the second end of the trunnion is tapered, wherein the head is partially spherical, and the annular shoulder is frustoconical, wherein the outer surface of the annular shoulder is tapered, and wherein the third bearing surface of the head is annular, and wherein the second end of the trunnion includes a pin that is received within the prosthesis stem, the pin centering the trunnion relative to the prosthesis stem when coupling the trunnion and the prosthesis stem.

* * * * *

UNITED STATES PATENT AND TRADEMARK OFFICE
CERTIFICATE OF CORRECTION

PATENT NO.       : 7,914,584 B2                       Page 1 of 1
APPLICATION NO.  : 11/255158
DATED            : March 29, 2011
INVENTOR(S)      : Bigsby et al.

It is certified that error appears in the above-identified patent and that said Letters Patent is hereby corrected as shown below:

Insert on title page item (30):

--(30)   Foreign Application Priority Data

Oct. 21, 2004   (GB)   GB 423415.9--.

Signed and Sealed this
Fifth Day of March, 2013

Teresa Stanek Rea
*Acting Director of the United States Patent and Trademark Office*